United States Patent
Battut

(10) Patent No.: US 6,323,502 B1
(45) Date of Patent: Nov. 27, 2001

(54) CHECKING THE ACCURACY OF FOLDING OF PARALLELEPIPED BOXES

(75) Inventor: Jean-Frederic Battut, Bron (FR)

(73) Assignee: Martin, S.A., Villeurbanne (FR)

( * ) Notice: Subject to any disclaimer, the term of this patent is extended or adjusted under 35 U.S.C. 154(b) by 0 days.

(21) Appl. No.: 09/247,260

(22) Filed: Feb. 10, 1999

(30) Foreign Application Priority Data

Feb. 19, 1998 (FR) .................................................. 98 02232

(51) Int. Cl.$^7$ .................................................. G01B 11/02
(52) U.S. Cl. .............................. 250/559.19; 250/559.24; 356/635; 493/12; 493/16
(58) Field of Search .................. 250/559.19, 559.24, 250/559.2; 356/635; 493/12, 13, 14, 15, 16, 18, 19, 25

(56) References Cited

U.S. PATENT DOCUMENTS 5,212,656  5/1993  Clary .

5,978,499 * 11/1999 Tossel et al. ..................... 382/141
5,993,367 * 11/1999 Hattori et al. .................... 493/12

FOREIGN PATENT DOCUMENTS 35 28 047 A1  2/1987  (DE) .
0 186 619 A2  2/1986  (EP) .

* cited by examiner

Primary Examiner—F. L. Evans
(74) Attorney, Agent, or Firm—Allen N. Friedman; McCarter & English LLP

(57) ABSTRACT

The method is disclosed for checking the accuracy of folding a parallelepiped box made from a cardboard blank (1) comprising four adjacent panels ($P_a$, $P_b$, $P_c$, $P_d$), at least some edges of the panels being associated with flaps ($R_{a1}$, $R_{a2}$, $R_{b1}$, $R_{b2}$, $R_{c1}$, $R_{c2}$, $R_{d1}$, $R_{d2}$) for closing the top and bottom surfaces of the box. Slots (5, 6) with parallel edges are formed between the adjacent flaps. In the method, the spacing between the edges of the slots (5, 6), produced between the flaps ($R_{a1}$, $R_{d1}$ $R_{a2}$, $R_{d2}$) when the outer panels are folded together, is compared with a predetermined standard spacing between the edges of the slots (5, 6) to determine whether the folded box is defective.

9 Claims, 2 Drawing Sheets

CHECKING THE ACCURACY OF FOLDING OF PARALLELEPIPED BOXES

RELATED APPLICATIONS

This application claims priority from French Patent Application France No. 98 02232, filed Feb. 19, 1998

GOVERNMENT FUNDED RESEARCH

Not Applicable

BACKGROUND OF THE INVENTION

1. Field of the Invention

The invention relates to a method, a device and use of the device for checking the accuracy of folding a parallelepiped box made from a cardboard blank

2. Brief Description of the Background Art

The blank that is used to form a cardboard box in the form of a parallelepiped comprises four adjacent panels extending between two opposite longitudinal parallel edges of the blank, the transverse sides of the panels being aligned along two parallel lines. One of the two opposite longitudinal parallel edges of the blank being formed with a gluing tab. At least some of the transverse sides of the adjacent panels are provided with flaps adapted to close the top and bottom surfaces of the box, folding lines being formed between the panels and also between the panels and the flaps. Slots having parallel edges are formed by folding the two side panels adjacent the opposite longitudinal edges of the blank on to the other two panels in order to join the opposite edges of the said blank so that the gluing tab overlaps the opposite edge.

SUMMARY OF THE INVENTION

If the folding lines between the adjacent panels of a box are not parallel, this will affect the parallelism between the adjacent edges of the slots formed by the flaps attached to the two panels adjacent the opposite two parallel edges of the cardboard blank, these edges being joined when the box is folded. The folding lines on a cardboard blank are defined by compressing the cardboard along the folding lines. Corrugated cardboard is more likely to have its faults, e.g. faulty parallelism between the folding lines, because of the corrugations which, if not exactly aligned with the compression lines, will cause the compression lines to overlap pairs of adjacent corrugations in the cardboard. In that case the fold may occur along a corrugation rather than along the compression line, resulting in a distortion in the shape of the box that is produced. This will affect the parallelism between the slots formed on the flaps adjacent the two panels of the cardboard blank that are being joined. It is therefore possible to detect folding errors in the box blank by measuring the width of the slot on each side of the folded panels and to compare the widths. This will be a measure of the defect in parallelism. The spacing between the adjacent edges of the slots will be greater between the flaps on one side of the panels than between the flaps on the opposite side of the panels. If the tolerance exceeds a certain amount fixed by the manufacturer in dependence on the type of packaging, the cardboard must be scrapped. The corrugations may also result in offsetting the position of the folding lines, which is unacceptable beyond a certain value. Measurement of the slot width also detects this error.

The object of the invention is specifically to detect the width of the two slots formed by the flaps adjacent the two end panels of the cardboard blank after the panels have been folded along the folding line, and to detect spacing beyond established norms, in order to eliminate defective cardboard boxes in accordance with an objective criterion established by the manufacturer. Unequal spacings detect nonparallel folding, while spacing that is wide or too narrow detects offset folding.

To this end the invention relates, firstly, to a method of checking the accuracy of folding a parallelepiped box as mentioned hereinabove. It also relates to a device for working the method and use of the device on a cardboard blank folding machine.

Since the folding lines between the four panels of the carton blank are parallel to the direction of travel of the blanks in the folding machine, the same applies to the slots formed between the flaps adjoining the end panels of the cardboard blank, the ends of which are joined after folding. It is therefore easy to measure the width of the slots during the motion of the folded cardboard blank in the machine. As will be seen, the measurement is preferably made employing a straight illuminated line produced by a beam of light projected at an angle to the plane of the blank, the thickness of the cardboard producing an offset between the part of the illuminated line falling in the slot and the rest of the illuminated line. This offset line is clearly displayed and can be easily measured.

In this way it is possible to check all cardboard boxes during the folding operation without wasting time by interrupting the flow of the folding machine. Consequently, the cost of the operation will be limited basically to the cost of the monitoring installation and adaptation thereof to each set of cardboard boxes. Preferably the device can be used together with a folding machine so as to automatically eliminate cardboard boxes that are not within the tolerances.

BRIEF DESCRIPTION OF THE DRAWINGS

The accompanying drawings, very diagrammatically and by way of example, show an embodiment of the method according to the invention.

DETAILED DESCRIPTION OF THE INVENTION

Since the folding machine is not part of the invention, the accompanying drawings do not show it but only the direction of travel 4 of the cardboard blanks 1 on the folding machine, together with a roller conveyor (T) of known kind, driven by a motor (not shown) for moving the cardboard blanks 1 on the folding machine.

Figure 1:
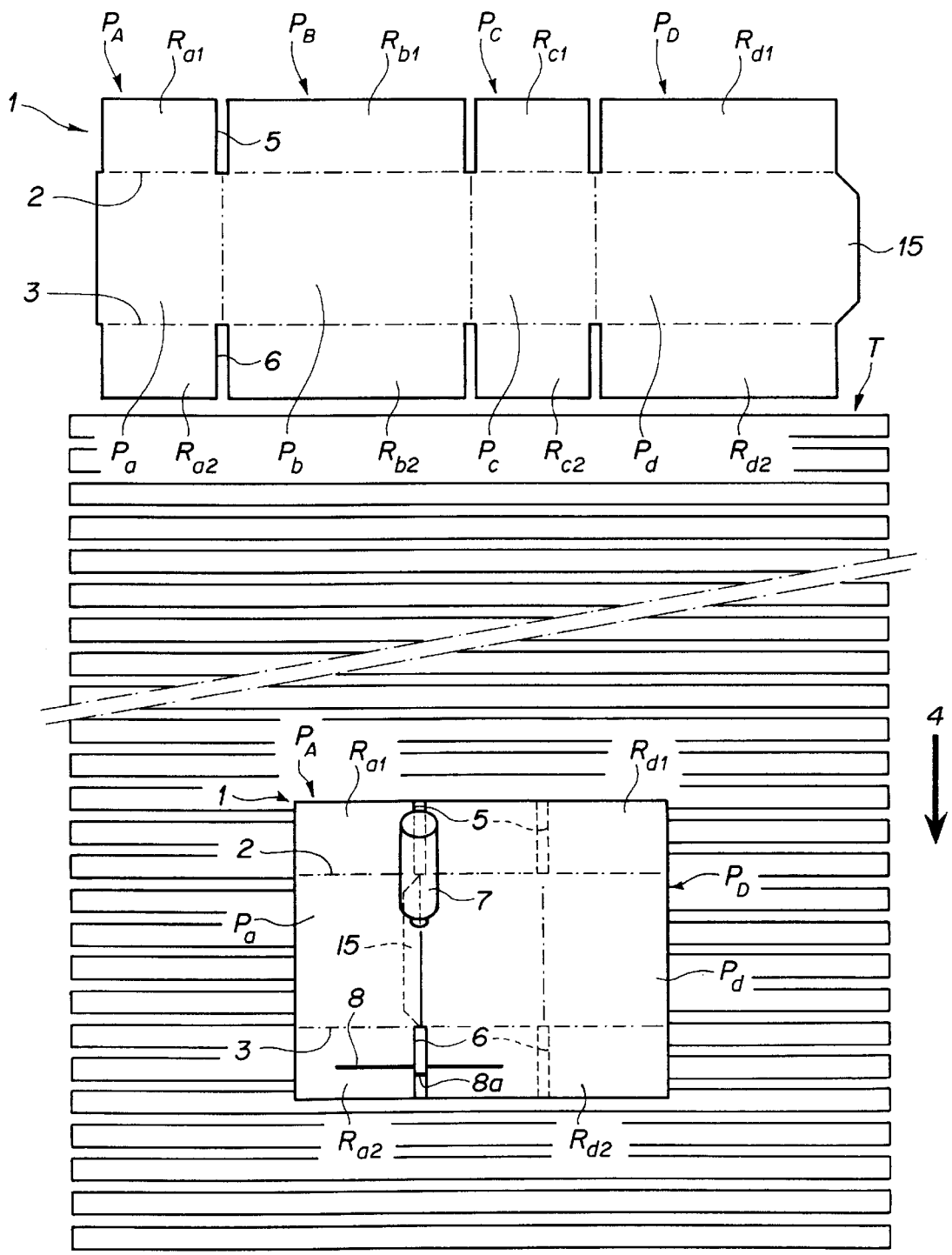
FIG. 1 illustrates a detection station for measuring the slots, an unfolded cardboard blank as it enters the folding machine, and a cardboard blank moving past the detection station after being folded.

FIG. 1 shows a cardboard blank 1 before folding, consisting of four adjacent panels $P_A$, $P_B$, $P_C$, $P_D$ extending between two opposite longitudinal edges parallel to the direction of travel 4 of the cardboard blank 1 on the conveyor T. FIG. 1 also illustrates the cardboard blank 1 after folding the two panels $P_A$, $P_D$ adjacent the two opposite longitudinal edges of the cardboard blank 1 onto the two central panels $P_B$, $P_C$. Two transverse parallel folding lines 2 and 3 extending across the direction of travel 4 of the cardboard blank 1 divide each panel $P_A$, $P_B$, $P_C$, $P_D$ into a panel $P_a$, $P_b$, $P_c$, $P_d$, and two adjoining flaps $R_{a1}$, $R_{a2}$, $R_{b1}$, $R_{b2}$, $R_{c1}$, $R_{c2}$, and $R_{d1}$, $R_{d2}$ respectively. Transverse line 2 is upstream of transverse line 3, line 3 being downstream. The panels $P_a$, $P_b$, $P_c$, $P_d$ are adapted to form the four side walls of the cardboard box, and the flaps $R_{a1}$, $R_{a2}$, $R_{b1}$, $R_{b2}$, $R_{c1}$, $R_{c2}$, $R_{d1}$, $R_{d2}$ are adapted to close the top and bottom surfaces of the box.

Slots 5 separate the flaps $R_{a1}$, $R_{b1}$, $R_{c1}$, $R_{d1}$ adjacent the folding line 2, whereas slots 6 separate the flaps $R_{a2}$, $R_{b2}$, $R_{c2}$, $R_{d2}$ adjacent the folding line 3. Only the slots 5 between the flaps $R_{a1}$, $R_{d1}$, and the slots 6 between the flaps $R_{a2}$, $R_{d2}$, formed in the folding operation, appear on the top of the folded cardboard blank 1. Two other slots 5 and 6 are covered by the panels $P_A$, $P_D$, and the other four are situated in the folds between the panels $P_A$ and $P_D$ respectively and are therefore visible only on the cardboard blank 1 as shown before folding.

The slots 5, 6 formed between the flaps $R_{a1}$, $R_{d1}$, and $R_{a2}$, $R_{d2}$ respectively result from joining the edges of the two panels $P_A$, $P_B$ after folding them over the other two panels. The width of these slots and the parallelism between the edges of these two slots 5 and 6 therefore depend on the accuracy of positioning and on the parallelism of the folding lines between panels $P_A$, $P_B$ and panels $P_C$, $P_D$ respectively. In order to hold the panels $P_a$–$P_d$ together after folding one end panel, e.g, $P_d$, has a gluing tab 15 which projects from the edge of the cardboard blank 1.

During folding, the cardboard blanks 1 are moved by the conveyor T, driven by its motor, and, thus, travel past the various working station is (not shown) on the folding machine. The outer edge of panel $P_a$ is folded after the panel $P_d$ is folded so that the gluing tab 15 is covered by the panel $P_a$. The bottom surface of panel $P_a$ or the top surface of the gluing tab 15 is coated with glue so that the two end panels $P_a$, $P_d$ of the cardboard blank 1 are fastened to one another after folding the end panels and, thus, joining the four side walls of the cardboard box.

Figure 2:
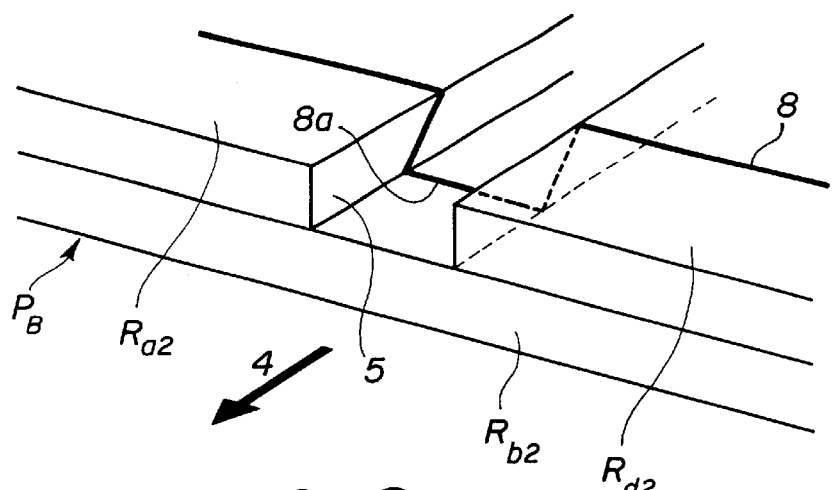
FIG. 2 is a larger-scale detail in perspective of a portion of FIG. 1, showing a part of the cardboard with its front (downstream) slot travelling through a beam of light which forms a line of light on its surface.

In order to show and display the width of the slots 5, 6 between the two flaps $R_{a1}$–$R_{d1}$ and the two flaps $R_{a2}$–$R_{d2}$, a line of light 8 is projected onto the cardboard blank 1 by a light source consisting, preferably, of a laser 7, the line of light being oriented perpendicular to the direction of travel 4 of the cardboard blank 1 driven by the conveyor T of the folding machine. The line of light 8 is from a light beam having its axis at an acute angle to the plane of the cardboard blank 1. Consequently, as shown in FIG. 2, because of the thickness of the cardboard blank 1, and because the light beam is inclined at an acute angle relative to the plane of the cardboard blank 1, the projected line of light 8 forms a segment $8_a$ on the blank 1 at the position of the slot 5 or 6, the part $8_a$ being offset parallel to the direction of traverse 4, relative to the portion of the line 8 falling on the panels $P_A$ and $P_D$.

If a camera 9 (FIG. 3) is placed with its optical axis, for example, perpendicular to the plane of the cardboard blank 1, i.e. with its optical axis at a defined angle to the axis of the laser 7 (preferably approximately 45 degrees), the camera 9 will form an image of the line of light 8 capable of showing the offset of the part $8_a$ of the light line. The optic axis of the camera 9 intersects the light beam at the line of light 8, forming the apex of the defined angle.

Figure 3:
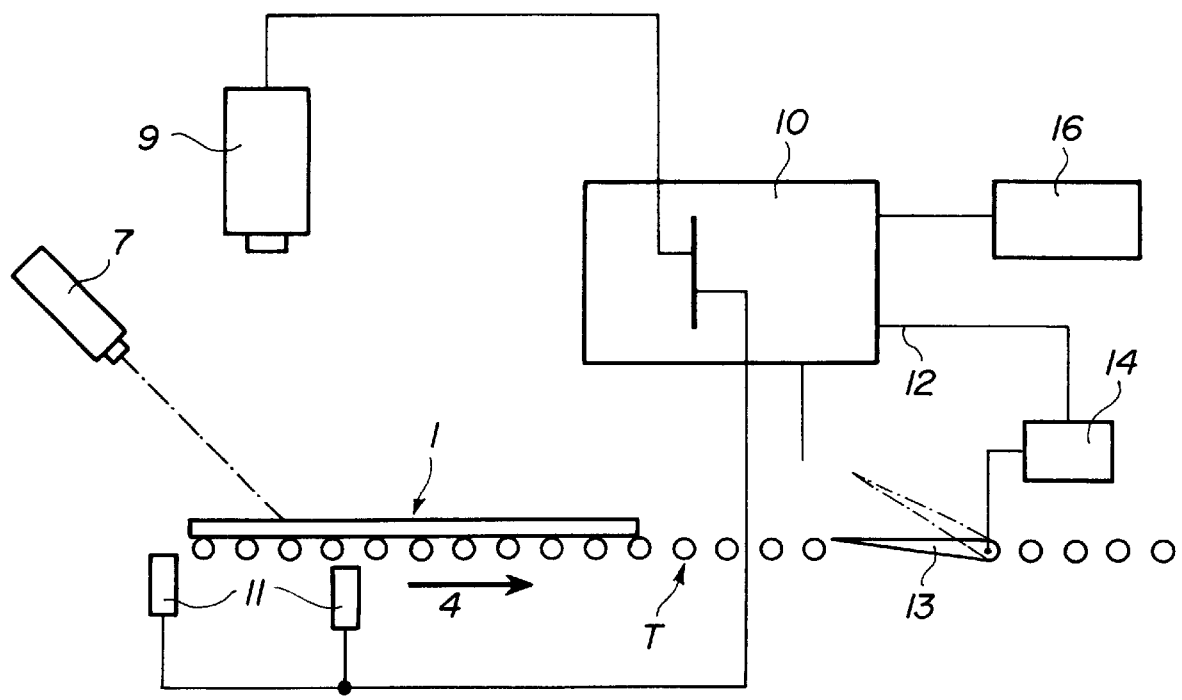
FIG. 3 is a schematic view of side elevation, relative to the direction of travel of the blanks on the folding machine, of a diagram illustrating the entire measuring system for working the method according to the invention and the device for ejecting defective boxes, under control of the measuring system.

As illustrated in FIG. 3, the camera 9 feeds its video signal to a computer 10. Two optical detection cells 11 are positioned to detect the slots 5, 6 at the front and at the rear respectively of the cardboard blank 1, relative to the direction of motion 4 of the cardboard blank 1 on the folding machine. The output signals of these optical detection cells 11 are also fed into the computer 10.

The computer 10 is equipped with image processing software, well known in the art, for recognizing the position of the slot on the image of the line of light that is transmitted by the camera 9 and for analyzing that image to measure the length of the line segment $8_a$ corresponding to the width of the slot. By means of the cells 11, the computer 10 also knows whether the measured slot is the front slot 5 or the rear slot 6.

The computer 10 is also connected by, for example, a RS232 connector to a co-ordinates box 16, used for transmitting counting data to the computer 10. The computer 10 also has an output 12 usable by a 24 V electronic system (API . . . ) and adapted to be activated whenever the slots in a cardboard blank 1 are outside the norms. The output 12 is connected to a device 13 for ejecting defective cardboard blanks 1. The ejection device 13 comprises a gate disposed along the path of conveyance through the folding machine, downstream of the slot-measuring device and actuated by an electromagnet 14 connected to the output 12 of the computer 10. If the measurements of the cardboard blank are outside the fixed minimum and maximum norms, the computer 10 sends an ejection command to the electromagnetic 14 and the electromagnet 14 raises the gate of the ejection device 13. The cardboard blank 1 is discarded by deflecting it below the conveyor T to a scrap area. The gate is then lowered and good boxes pass over it and downstream on the conveyor T.

An exemplary measuring device of the invention is adapted to read and measure the front and rear slots 5, 6 on the moving blanks, up to five blanks per second. The size of the blanks in the direction of motion may vary from 255 to 920 mm. The gap between the front and rear edges of two successive cardboard blanks 1 on the folding machine, in the state where the blank 1 is illustrated in FIG. 1, is 1100 mm. The information relating to the ejection command, given in the form of a pulse at output 12, is calibrated at about 100 ms and is activated in a very short time (<80 ms) after acquisition of two images relating to the front slot 5 and the rear slot 6 of a cardboard blank 1. These quantities are varied by the process controller in accordance with the velocity of the conveyor T and the folding rate of the folding machine.

Of course the function of the computer 10 is not exclusively limited to the command to eject defective cardboard blanks 1. Like any computer, it can be used to compute various statistics based on of the measurements made.

As shown by the arithmetic data relating to the speed of measurement and of control of the device for ejecting defective cardboard blanks 1, the rate of measurement is perfectly compatible with the speed of the folding machine, so that the measurement does not involve any increase in the production cost through use of additional staff or by the need to slow down the production rate. Consequently, the only investment to be taken into account is for the measuring device, and this can quickly be recovered in view of increased reliability regarding product quality. As mentioned, since each cardboard box is measured, the result is a check on the total production and the measurements can also be used to prepare statistics enabling other improvements to be made, since the statistics may show the unknown or little-known effect of certain parameters on the accuracy with which cardboard blanks are folded.

What is claimed is:

1. A method for checking the accuracy of folding a parallelepiped box made from a cardboard blank (1) comprising four adjacent panels $P_a$, $P_b$, $P_c$, $P_d$ extending between two opposite parallel longitudinal edges of the cardboard blank (1), the panels' ($P_a$, $P_b$, $P_c$, $P_d$) transverse sides being aligned along two parallel transverse lines (2, 3), one of the two opposite parallel longitudinal edges of the cardboard blank (1) being provided with a gluing tab (15), at least some of the transverse sides of the adjacent panels ($P_a$, $P_b$, $P_c$, $P_d$) being provided with flaps ($R_{a1}$, $R_{a2}$, $R_{b1}$, $R_{b2}$, $R_{c1}$, $R_{c2}$, $R_{d2}$, adapted to close the top and bottom surfaces of the box, longitudinal folding lines being formed between the panels ($P_a$, $P_b$, $P_c$, $P_d$) and transverse folding lines being formed between the panels and the flaps ($R_{a1}$, $R_{a2}$, $R_{b1}$, $R_{b2}$, $R_{c1}$, $R_{c2}$, and $R_{d1}$, $R_{d2}$), slots (5, 6) having parallel longitudinal slot edges being formed between the adjacent flaps ($R_{a1}$, $R_{a2}$, $R_{b1}$, $R_{b2}$, $R_{c1}$, $R_{c2}$, and $R_{d1}$, $R_{d2}$), the box being formed by folding two side panels ($P_a$ $P_d$) adjacent the opposite longitudinal edges of the cardboard blank (1) onto the two central panels ($P_b$, $P_c$) in order to join the opposite longitudinal edges of the cardboard blank (1) so that the gluing tab (15) overlaps, forming a junction, the method comprising measuring the spaces between the slot edges of the slots (5, 6) of the flaps ($R_{a1}$, $R_{d1}$, $R_{a2}$, $R_{d2}$) situated on either side of the junction and comparing the measured spaces between the flaps ($R_{a1}$, $R_{d1}$, $R_{a2}$, $R_{d2}$) with a predetermined standard spacing between the flaps ($R_{a1}$, $R_{d1}$, $R_{a2}$, $R_{d2}$) in order to determine whether the box is a defective box.

2. A method of claim 1, wherein the slots (5, 6) are moved in a direction (4) parallel to the longitudinal slot edges of the slots (5, 6); a light source (7) is situated so that its direction of radiation is at an acute angle to the plane of the cardboard blank (1); and a line of light (8) transverse to the direction of travel (4) is projected on the surface of the cardboard blank (1), intersecting the edges of the slots (5, 6), so that an offset portion (8a) of the line of light (8) corresponding to the spacing between the edges of the slots (5, 6) is offset and the width of the offset portion (8a) is measured.

3. A method of claim 2, wherein a beginning point and an end point of travel of the slots (5, 6) along the direction (4) is detected.

4. A method of claim 2, wherein the line of light (8) projected onto the cardboard blank (1) is measured from an observation point at a defined angle to the direction of radiation, the apex thereof coinciding substantially with the line of light (8).

5. A device for working the method according to claim 1, comprising:

(a) a light source (7) situated so as to radiate in a direction at an acute angle to the plane of the cardboard blank (1) and which is adapted to form a line of light (8) across the edges of the slots (5, 6);

(b) observation means (9) for observing the line of light (8) and situated so that its optic axis forms a defined angle relative to the direction of radiation of the said light source (7) with its apex at the line of light (8);

(c) means (T) for moving the slots (5, 6) relative to the observation means (9) on the one hand and the light source (7) on the other hand in a direction of traverse (4) parallel to the edges of the slots (5, 6); and (d) means (10) for measuring a length of an offset portion (8a) of the line of light (8) to produce a slot width measurement.

6. A device of claim 5, comprising a first detection cell (11) for detecting a slot (5) situated on the panel's ($P_a$, $P_b$, $P_c$, $P_d$) upstream side and a second detection cell (11) for detecting the slot (6) situated on the panel's ($P_a$, $P_b$, $P_c$, $P_d$) downstream side.

7. A device of claim 5, comprising a computer (10) for comparing the slot width measurements of the slots (5, 6) with a predetermined standard slot width measurement in order to determine whether the box is a defective box.

8. A device of claim 7 comprising means for energizing a deflecting gate (13) to deflect a defective box from the direction of travel (4).

9. Use of a device of claim 7 in combination with a machine for folding cardboard box blanks (1), wherein the folding machine comprises ejection means (13) connected to the computer (10) for comparing the slot width measurements between the edges of the said slots (5,6) with a predetermined slot width measurement so as to eliminate the defective box in response to a result of the comparison.

* * * * *